United States Patent
Le Gargasson et al.

(10) Patent No.: US 6,470,124 B1
(45) Date of Patent: Oct. 22, 2002

(54) DEVICE FOR OBSERVATION INSIDE A BODY PROVIDING IMPROVED QUALITY OF OBSERVATION

(75) Inventors: Jean-François Le Gargasson, Villiers S/Marne; Frédéric Lamarque, Les Essarts le Roi; Jean-Paul Chaduc, Clermont Ferrand, all of (FR)

(73) Assignees: Assistance Publique - Hopitaux de Paris, Paris (FR); Institut National de la Sante et de la Recherche Medicale (INSERM), Paris (FR)

(*) Notice: Subject to any disclaimer, the term of this patent is extended or adjusted under 35 U.S.C. 154(b) by 0 days.

(21) Appl. No.: 09/787,176
(22) PCT Filed: Sep. 15, 1999
(86) PCT No.: PCT/FR99/02188
§ 371 (c)(1), (2), (4) Date: Jun. 8, 2001
(87) PCT Pub. No.: WO00/16151
PCT Pub. Date: Mar. 23, 2000

(30) Foreign Application Priority Data

Sep. 15, 1998 (FR) .............................................. 98 11486

(51) Int. Cl.[7] ................................................. G02B 6/06
(52) U.S. Cl. ..................................... 385/117; 600/167
(58) Field of Search ............................ 385/117; 600/167, 600/182

(56) References Cited

U.S. PATENT DOCUMENTS

| | | | |
|---|---|---|---|
| 4,821,117 A | * | 4/1989 | Sekiguchi ..................... 348/68 |
| 5,074,642 A | | 12/1991 | Hicks |
| 5,103,497 A | | 4/1992 | Hicks |
| 5,120,953 A | * | 6/1992 | Harris ......................... 250/216 |
| 5,280,378 A | | 1/1994 | Lombardo |
| 5,425,123 A | | 6/1995 | Hicks |
| 5,575,757 A | * | 11/1996 | Kennedy et al. ............... 348/65 |
| 5,630,788 A | * | 5/1997 | Forkner et al. ............. 385/117 |
| 6,111,645 A | * | 8/2000 | Tearney et al. ............. 356/484 |

FOREIGN PATENT DOCUMENTS

| | | |
|---|---|---|
| DE | 42 07 092 A1 | 9/1993 |
| JP | 61251819 | 11/1986 |
| JP | 04038092 | 2/1992 |

* cited by examiner

Primary Examiner—Neil Abrams
Assistant Examiner—Brian S. Webb
(74) Attorney, Agent, or Firm—Young & Thompson

(57) ABSTRACT

The invention concerns a device for observation inside a body, such as the body of a living being, comprising means for illuminating (110, 115, 200, 300, 400) the body inside, means for displaying an image (600, 700, 800), and a flexible conduit (300) for travelling through an inside part of the body and conveying an image from inside the body to the displaying means (600, 700, 800), the illuminating means (110, 115, 200, 300, 400) being arranged to automatically scan a zone of the body forming the displayed image.

16 Claims, 2 Drawing Sheets

FIG_1

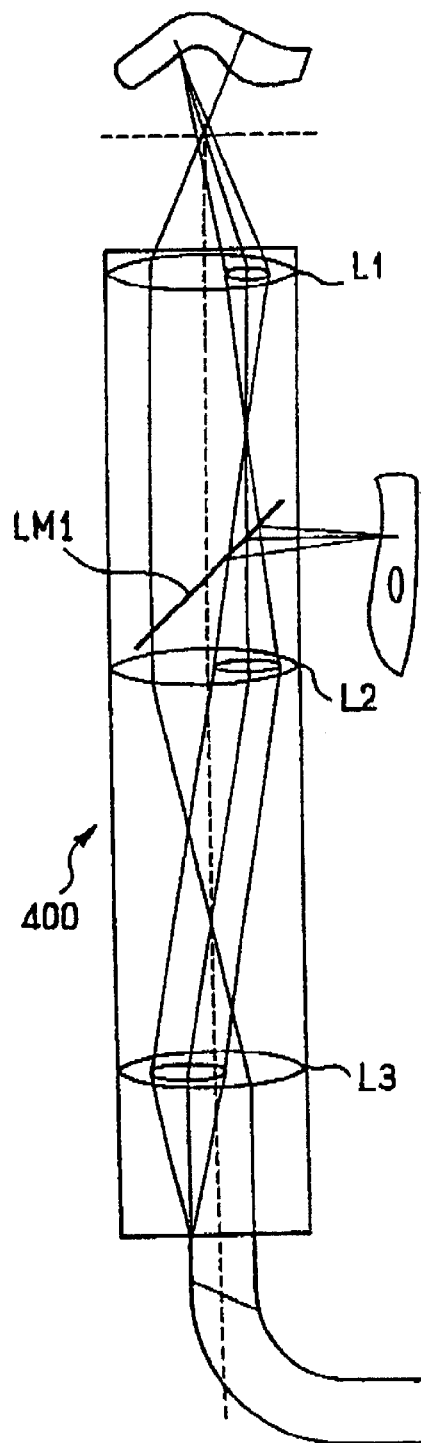
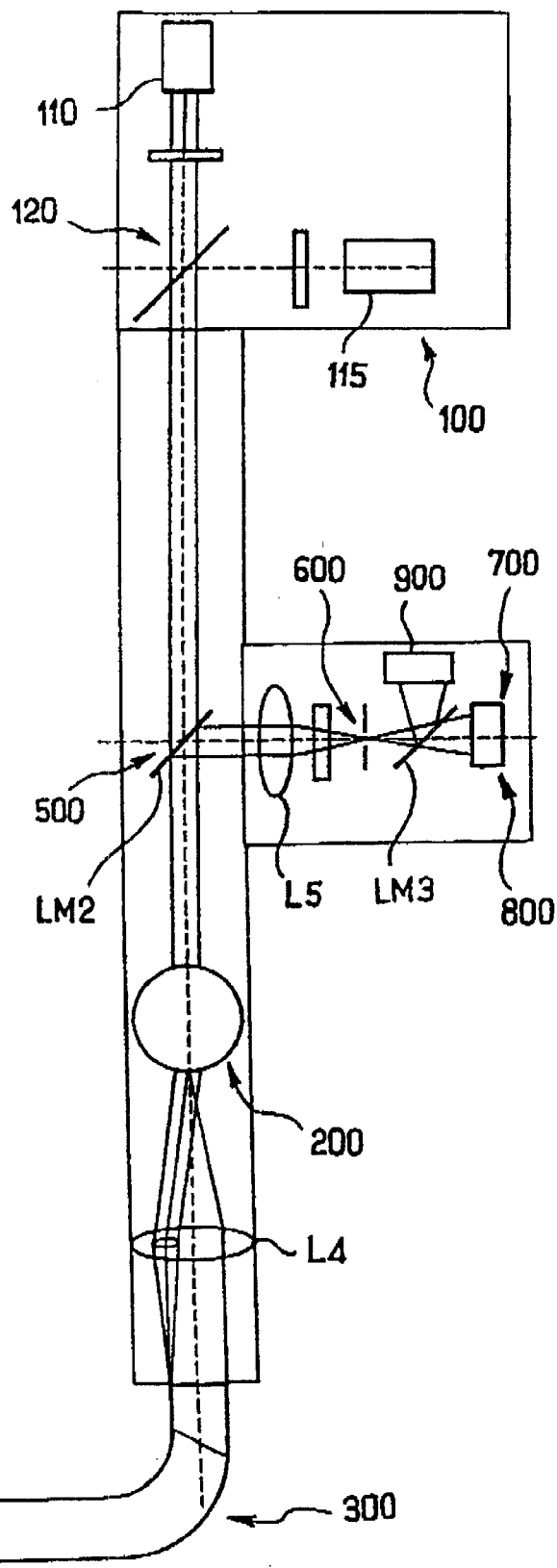
FIG. 2

DEVICE FOR OBSERVATION INSIDE A BODY PROVIDING IMPROVED QUALITY OF OBSERVATION

BACKGROUND OF THE INVENTION

The present invention relates to devices for observing the interior of a body, living or manufactured, comprising a flexible conduit for transmitting images from the interior of the body to an image display device that is outside of the body. In these devices, the flexibility of the conduit makes it possible to pass through a part of the body, linking a zone to be observed that is inside the body, to an external viewing console.

The conduit must be flexible enough for it to penetrate into regions of the body that may be particularly convoluted.

Usually the conduit must also be sufficiently rigid to permit guiding of an examination tip of the conduit, from outside the body, by action on the conduit.

In many devices of this type, the conduit is manipulated in order to gain access, at an illumination end of this conduit, adjacent to the body, to a region for observation within the body which is inaccessible directly from outside the body with photon radiation.

These devices therefore usually constitute means for examining regions that are inaccessible to direct observation.

When the body to be observed is the body of a living being, such devices are generally called endoscopes.

The known endoscopes are often based on a principle of overall illumination of a field, in poly- or monochromatic light. Light is transmitted via an illumination channel, and the visual information is transmitted through another channel.

With these endoscopes, observation is by means of a photographic sensitive surface or a CCD camera. They therefore require high levels of illumination.

Their performance level is determined essentially by the optical resolution of a system for carrying the images and by the quality of an optical system. They do not permit observations to be made with satisfactory depth resolution, nor do they give acceptable contrast, especially in diffusing environments.

Furthermore, these devices are unable to provide, simultaneously, a large viewing field and a wide numerical aperture in a confined space.

An endoscope has also been proposed, in document U.S. Pat. No. 5,074,642, comprising a bundle of fibres of which the end towards the observer is positioned opposite a light source and is vibrated opposite this light source, the various fibres are scanned by the source, and scanning of a region of the body is thus obtained.

Such a device only permits very slow scanning of the fibres and in particular proves to be too slow for obtaining a video image in real time.

In the field of microscopy, devices called "confocal microscopes" have been proposed. These devices cannot be used for endoscopic examination. Confocal microscopes are used for various types of microscopic examination, such as examination of sections by transillumination, or direct anatomical observation by back-illumination, or investigation with the aid of dyes such as fluorescein, indocyanine green or acridine orange.

SUMMARY OF THE INVENTION

With certain recent experimental systems, functional investigations are also possible, such as investigation of functional activities of the cerebral pathways or evaluation of the condition of vessel walls. However, observation of cerebral neurologic activity, for example, can only be carried out on animals, as it is necessary to carry out an ablation of the top of the skull to mount a confocal microscope for observation.

Document DE 42 07 092 also proposes an endo-scope that has a bundle of optical fibres for conveying an image from the observed object to the observer. This document proposes means for scanning a beam in this grating of fibres, but this bundle is used solely for a therapeutic treatment and not for illuminating a region for the purpose of observation. The illumination is an overall illumination.

One aim of the present invention is to propose a device for viewing the interior of a body, such as the body of a living being, comprising means for illuminating the interior of the body, a means of displaying an image, and a flexible conduit that is to pass through an internal region of the body and convey an image from the interior of the body to the display means, which provides a particularly clear image of an observation region inside the body (by confocal techniques or by techniques based on interferometry).

Another aim of the present invention is to propose a device of the endoscope type giving acceptable depth resolution and contrast, even in diffusing media under observation.

Another aim of the invention is to propose an endoscope with high photon sensitivity.

Another aim is to propose a device permitting spatial and temporal separation of the parasitic flux associated with the illumination of that corresponding to tissue reflection.

Another aim is to propose a device that limits reflection in overlying and underlying diffusing media of a tissue medium being examined.

Another aim is to propose a device that makes it possible to eliminate reflections associated with optical mounting elements.

The invention also aims to propose a device that permits the formation of a tissue image with a wide-aperture exploratory light beam by placing the optical device in contact with or a few millimetres away from the tissues or surfaces to be examined.

According to another aim, the invention proposes a device that can withstand possible vibration of the mounting and does not require special maintenance or adjustment.

Another aim of the invention is to supply a device that can provide a satisfactory resolution with a group of fibres of small diameter.

A further aim of the invention is to supply a viewing device that does not have, in its part adjacent to the body being examined, any electronic or mechanical part that is likely to be attracted or damaged when submitted to an intense magnetic field, so that it can be used in conjunction with a device for observation by magnetic resonance.

It also aims to permit particularly rapid scanning of optical fibres.

These various aims are achieved by means of a device for observing the interior of a body, comprising a means of displaying an image, a group of fibres gathered together side by side and intended to pass through an internal part of the body to convey an image from the interior of the body to a display means, illumination means provided for scanning the fibres of the group of fibres, positioned at the end of the fibres that is farthest from the body, characterized in that the illumination means include means for imparting successive angular deflections to an illumination beam, means for converting the angular scan obtained to a lateral scan relative to a principal axis of entry of the group of fibres, in that the means for scanning the fibres are external to the group of fibres and in that the group of fibres forms an image guide whose ends are arranged in the same order at both ends of the guide.

BRIEF DESCRIPTION OF THE DRAWINGS

Other characteristics, aims and advantages of the invention will become evident on examination of the following detailed description and of the appended drawings in which:

FIG. 2 is a more detailed view of an endoscope conforming to the scheme in FIG. 1.

DESCRIPTION OF THE PREFERRED EMBODIMENTS

Figure 1:
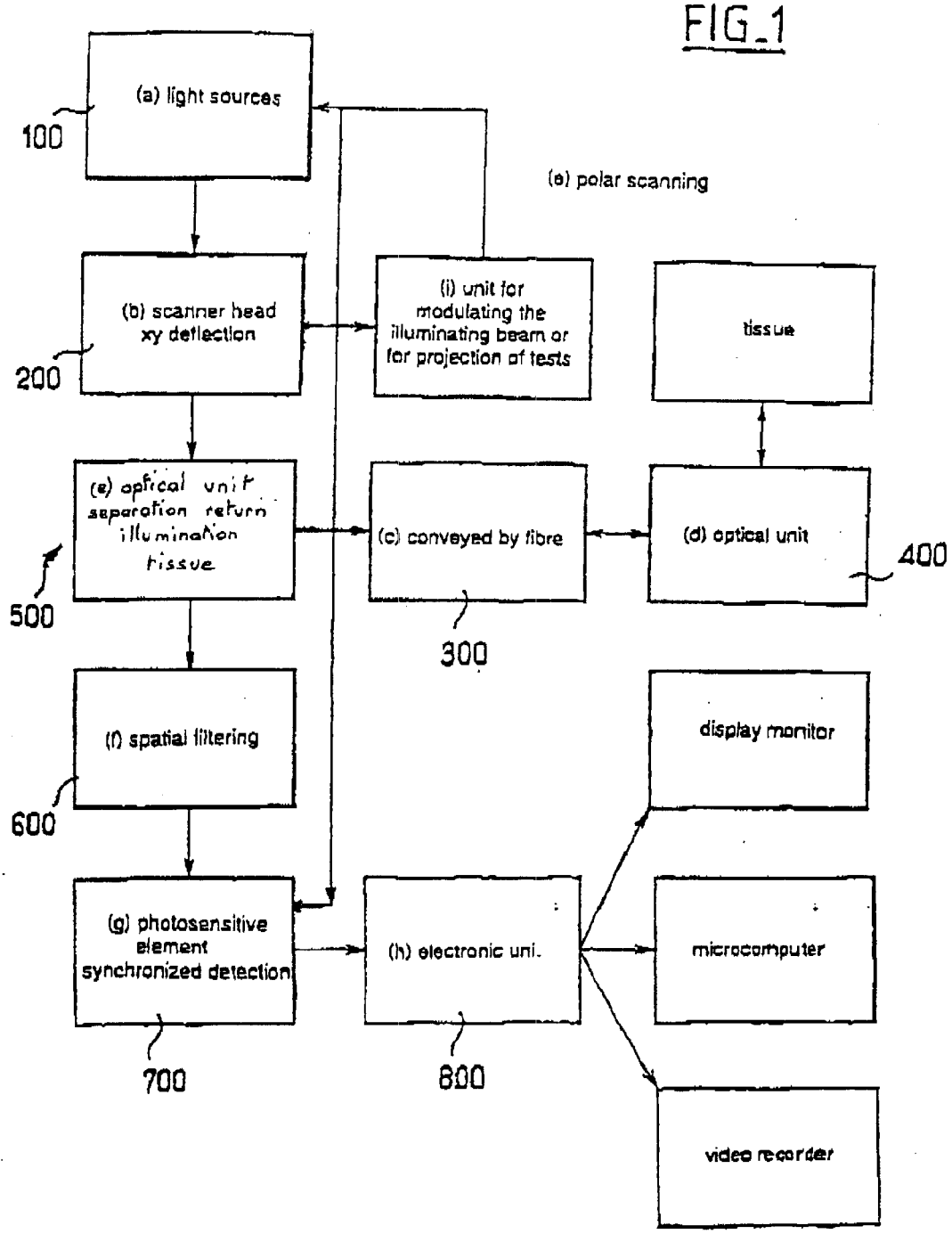
FIG. 1 is an overall view in the form of functional units of one embodiment of a device according to the invention.

The device in FIGS. 1 and 2 has eight main parts: a light source unit 100, a scanning unit 200, an image transport module 300, a front optical unit 400, a rear optical unit 500, a spatial filtering unit 600, a unit for converting an optical signal to an electrical signal 700, and an electronic unit 800.

The light source unit 100 produces light by means of a low-power laser source 110 and by a visible light source 115. Illumination can be provided by a laser beam of visible or infrared wavelength.

These two sources have directions of emission that are perpendicular to each other, a dichroic mirror 120 being placed at 45° from the direction of emission of the source of visible light to deflect the latter in a direction parallel to the direction of emission of the laser source 110. This mirror 120 is selected so that it has no deflecting effect on the rays emitted by laser source 110. These two sources can be sources of the xenon arc lamp type, or alternatively incandescent sources.

The choice of set-up and of the characteristics of the sources used depends on the type of application. Thus, the short wavelengths and the infrared radiation permit excitation of fluorescein and of indocyanine green, respectively. The infrared beams also make it possible to observe deep tissue layers whereas the visible wavelengths clearly reveal the layers nearest the surface.

The intensity of the various sources is selected to be compatible with the safety regulations concerning the destruction of biological tissues, i.e. in particular AFNOR standard C43-801, 1992 and ANSI standard Z136.1, 1993.

The source device described here permits mixing of the two sources, laser and visible, as well as adjustment of the power of the beam from each of them. A modulator, controlled by an electronic or optical device, is placed in front of each of these two sources 110 and 115 and makes it possible to produce trains of light pulses which will permit synchronous detection of a reflected flux while eliminating reflections, as will be described later. Pulse trains can be generated by direct control of the illumination and detection elements.

In the particular example described in FIG. 2, tissue is illuminated in the infrared. The illumination flux is generated by an infrared laser diode emitting at a wavelength of about 800 nm.

More generally, the light source unit 100 can comprise one or more laser sources and/or source of incoherent monochromatic light and/or incoherent polychromatic light.

Downstream from this light source unit, relative to the path of the light emitted, there is the scanning unit 200, consisting of a deflector of the light rays emitted by the source 100.

Downstream from this scanning unit, a lens L4 is arranged, followed by a group of flexible optical fibres 300, parallel to one another. The group of optical fibres 300 or image guide has the ends of its fibres adjacent to lens L4 in a plane parallel to this lens.

The scanning unit 200 is made up of optical elements, which are opto-acoustic optical elements in the particular example of embodiment described here.

According to a variant of the invention, these elements can be opto-mechanical elements.

The role of the assembly of scanning unit 200 and lens L4 is to deflect the beam emitted from the light source 100 in horizontal and vertical directions, in order to scan the entry section of the fibre-optic image guide 300.

Scanning unit 200 therefore produces successive angular deflections of the illuminating beam from source 100. These angular deflections are converted by lens L4 into a lateral deflection focused on the entry section of the fibre-optic image guide 300, thus producing successive illumination of the various optical fibres of the group of fibres 300. Thus, to each optical fibre there corresponds one angle of deflection of the illuminating beam and just one at the outlet of scanning module 200.

Each beam, after angular deflection, is redirected by lens L4 onto a beam having a constant direction relative to a principal entry axis of image guide 300, here approximately parallel to the principal entry axis of image guide 300.

Such a beam, redirected according to a chosen direction that is roughly constant, which may or may not be parallel to the principal entry axis of the group of fibres, has, in the course of scanning, a lateral position relative to the principal entry axis of the guide that corresponds to a selected fibre of the group of guides.

We therefore obtain, downstream from lens L4, scanning that is lateral to the entry axis of the guide, i.e. at the entry axis of the guide, a lateral displacement of a beam having a constant direction, in this case a direction parallel to this axis. This lateral scanning is obtained by the action of lens L4 starting from upstream angular scanning, the said angular scanning being implemented with apparatus that takes up little space and is particularly fast.

Redirection of the rays in a constant direction can also be achieved with an optical assembly of the microscope objective type. Thus, by interaction of scanning unit 200 and lens L4, we obtain an optical system that is able to form a focal point in an entry interface plane of the image guide 300.

Lens L4 therefore makes it possible to convert the angular scanning of the illuminating beam into a translational scanning, so as to impinge on the optical fibres at a constant angle, normal to their cross-sections.

The optical fibres are therefore addressed in the course of time in such a way that at a given moment one, or an assembly of fibres, carries the illumination flux to the other end of the fibre-optic image guide.

Even more precisely, in the example of application described here, the beam issuing from source 100, which is collimated, is deflected in X and Y by unit 200, which is an opto-mechanical device comprising a servo-control galvanometer and an oscillator that resonates at 8 kHz. Lens L4 has a focal length of 2.8 mm.

In the case of polychromatic illumination, optical deflection must be effected by an opto-mechanical system. When using a laser beam or a monochromatic incoherent source for illumination, optical deflection can also be effected by a two-dimensional opto-acoustic deflector located at a suitable distance to ensure scanning of the entire surface of the entry interface of the fibre-optic image guide.

If the sources used are monochromatic incoherent sources, deflection can be obtained by means of a two-dimensional opto-acoustic deflector or by means of two one-dimensional opto-acoustic deflectors. Such a device has the advantage that it has no moving mechanical parts. The opto-acoustic deflectors are sensitive to the wavelength. In such devices it will therefore be advisable to provide a deflector for each wavelength used.

When the deflectors employed are opto-mechanical deflectors, horizontal deflection can be obtained either by means of an opto-mechanical resonating mirror, or by means of a rotating motor equipped with a faceted polygonal mirror, or by means of a galvanometric mirror. Vertical deflection can be obtained by means of a galvanometric device possessing a spindle equipped with a mirror.

This device therefore makes it possible to form an image of the source that is less than or equal in diameter, to the diameter of the cross-section of an optical fibre, in the plane of the entry interface of the fibre-optic image guide 300.

The assembly comprising the source, unit 200 and lens L4 can be replaced by a photo-emitting active matrix. Such a matrix can be under sequential electric or photon control. In certain arrangements, source unit 100 can be coupled directly to the fibre-optic image guide (especially in the case of a therapeutic laser).

Image guide 300 is made up of a group of optical fibres arranged in the same order at the entry and output interfaces of this group of fibres. Within the group, the optical fibres are arranged according to an arrangement that is identical at both ends of the image guide.

Accordingly, scanning of the group of fibres effected at the observer's end occurs on the same path transverse to the fibres at the body end of the group of fibres.

Since the light is taken, at the observer's end, from the successive fibres in the course of this scanning, light gathering scanning also follows the same transverse path as the scanning of the region.

The means for illumination and light gathering located at the observer's end of the group of fibres illuminate and gather light from the end of the group of fibres as if it were the region of the body to be examined, so that the group of fibres, owing to its ordered nature, produces, on the basis of these means, image transport from the body to the end of the guide adjacent to these means, and each point of this image, i.e. each fibre, has the same position in the transported image at the entry as at the output of the guide.

In the prior art, the proposed observation devices generally make use of just an assembly of fibres without perfect correspondence between the surface of. the imaged field and the transverse surface of what is then called a bundle of fibres, even apart from the optical magnification.

In the embodiment described here, the area of the output interface of the fibre-optic image guide is equal to the field of observation or imaged area of the tissue under examination, apart from the optical magnification of an optical system placed between the output interface of the fibre-optic image guide and the tissue under examination.

In the case described here, the image guide consists for example of a group of 10 000 fibres arranged as a square with a side of 100 fibres. It would also be possible to make an image guide having for example a square of 800×600 fibres, or more.

More precisely, the fibre-optic image guide is made up of 100×100 contiguous optical fibres with diameter of 4.5 $\mu$m and numerical aperture of 0.35. In the present case this fibre-optic image guide has a length of 10 meters. The recommended minimum value of 2 meters makes it possible to avoid a shadow cone effect at outlet from the fibre.

The end of the optical fibre directed towards the body to be observed is arranged in the focal plane of a lens L3, belonging to the front optical unit 400.

The front optical unit 400 comprises the outlet end of the fibre-optic image guide 300, then, along a light path, a first lens L3, a second lens L2, a plate LM1 and a lens L1 are propagated successively towards the body to be observed.

The outlet end of the image guide is mounted on optical unit 400, this unit preferably being movable relative to this outlet interface of the guides. As has already been described, optical scanning of the group of fibres by unit 200 has the effect of illuminating each of the optical fibres of unit 300 successively. The outlet of each fibre will therefore form a secondary light source at a given instant, and this light source moves linearly from fibre to fibre.

As this secondary light source is in the focal plane of lens L3, this transverse movement of the secondary light source is converted to an angular deflection by lens L3. Lens L2 and lens L3 have a common focus that is located between these two lenses, in such a way that the angular deflection at the outlet of lens L3 is converted again by lens L2 to a transverse deflection.

Lens L1 then deflects this beam onto a beam focused on a point of the plane conjugate with the focal plane of lens L2. Lens L1 focuses the beam in the plane of the body to be observed. This point of concentration of the outlet beam passes through a plane of illumination of the body to be observed when the fibres of the group of fibres are illuminated successively. The luminous flux reflected by each point of the illuminated body forms, on passing through lens L1, a point image on the illumination fibre with the aid of lenses L2 and L3. Accordingly, each optical fibre performs the role of a spatial filter successively.

Means 400 are therefore provided to make different positions of the focal point correspond to the different fibres of the group of fibres 300, according to a relation such that the point of concentration effects scanning of the region to be observed when the fibres are swept by the illumination device.

In the particular example of embodiment described here, lens L3 has a focal length of 2.8 mm. It collimates the outlet beam from the fibre and converts the scanning in translation from fibre to fibre, to an angular scanning of the illumination beam, whose centre of rotation is located in the focal plane of the afocal system L2–L3. The focal lengths calculated for L3 and L2 permit scanning of a tissue field to be observed of 10°×10° by an illumination spot of the order of 2 $\mu$m.

Focusing of the observation plane in the tissue plane that we wish to observe is obtained by moving the end of the optical fibre relative to lens L3.

Movements of the device made up of the three lenses L1, L2 and L3, or of certain particular lenses of this device, make it possible more generally to vary the position of the confocal illumination plane of the tissue. The aperture of the optical fibre, and the respective focal lengths of the lenses of optical unit 400, determine the aperture of the illumination beam and the value of the tissue field examined. Unit 400 is therefore movable and interchangeable in relation to the image transport system.

On the fibre side adjacent to the body, a plate LM1 is arranged between lenses L1 and L2. This plate LM1 is a return plate arranged at 45°, reflecting a series of wavelengths laterally to unit 400 and permitting lateral viewing of tissue sections. Lens L1 can be an assembly of lenses permitting widening of the field of view given by lens assembly L3 and L2 or groups of lenses, plate LM1 makes it possible to obtain, simultaneously, axial and lateral views with different field of view and magnification, respectively.

It is preferable to choose a plate LM1 that is sensitive to chromatic aberration and that can be changed depending on the use and the wavelengths employed for the said lateral visualization.

With such a device it is possible to obtain an axial view and a lateral view simultaneously.

In a most advantageous device, plate LM1 reflects the infrared wavelengths and a visible wavelength, at 45°, but allows the rest of the spectrum to pass through along the axis of unit 400, in the direction of the image guide.

Plate LM1 reflects, at 45°, the infrared wavelengths (830 nm, 800 nm) and one or more visible wavelengths (for example, wavelengths of 680 nm, 514 nm, 477 nm). The said plate LM1 allows the other wavelengths to pass. Plate LM1 therefore makes it possible to view images laterally with a small field and high resolution, and axial images with a large field and lower resolution.

Thus, in this device, one of the image display devices is able to supply a view of a general region and the other is able to supply a confocal microscopic view of a more restricted region, which may or may not be contained within the general region.

The two image display devices are moreover able to supply a microscopic image and a macroscopic image simultaneously.

The set-up described above permits focusing on different planes of tissues being examined. This adjustment of the position of the illumination plane and observation plane, i.e. of the confocal observation plane of the tissues, is obtained either by moving the outlet interface of fibre-optic image guide 300, i.e. the interface located on the tissue side, relative to optical unit 400 which in this case remains fixed and is located in front of the tissue, or by moving the assembly of lenses L1, L2 and L3 according to the state of the art in order to change the focal plane of focusing in the body while keeping the examination field constant.

In this second case, examination by tomography can be carried out without altering the tissue field examined on the one hand, and without altering the numerical aperture on the other hand. These independent movements of the diameter of the outlet interface of the image guide, i.e. of the filtering element as will be described below, mean that the position of the body being examined and the thickness of the tissue section being examined can be chosen independently.

The optical section located at the end of the image guide on the observed tissue side therefore provides illumination of tissue micro-surfaces. The flux reflected by this small area of tissue illuminated for a brief instant assumes the inverse path of the illumination flux. Thus, the rays reflected and backscattered by the illuminated micro-surface pass successively through lens L1, plate LM1, lens L2, lens L3, the fibre-optic system of the group of fibres that is illuminated for this brief instant, then this observation beam passes again through the opto-mechanical scanning device 200, where it is stabilized.

The observation beam then arrives on a dichroic plate LM2 set at 45° in the path of the mixed illumination and observation beam between the deflector 200 and the source 100. This plate LM2 is chosen to allow passage of the illumination flux going from source 100 to the optical fibres and to reflect, at 90°, the observation rays coming from the optical fibres.

Plate LM2 located on the observer side relative to the fibres is therefore intended to ensure separation between the illumination beams and the light backscattered by the tissues being examined. According to an advantageous arrangement of the invention, plate LM2 is a separating plate whose characteristics vary as a function of the wavelength. Just as with plate LM1 described previously, plate LM2 can be replaced by a prism or a cube that is able to separate rays that have opposite directions of propagation.

The simplest device for separating the illumination and detection pathways is constituted by this plate LM2 favouring the flux emitted from the tissues. Any other device capable of separating the illumination flux from the flux that is backscattered by the tissue could be used as a replacement for the said plate LM2. Thus, interference filters can be interposed in the detection pathway in the case of a fluorescence image. It is also possible to employ separation by means of a polarization separating device by using a polarized illumination source. The said device will be useful for studying the autofluorescence of tissues or the fluorescence emanating from a dye that circulates and/or is fixed in tissues excited by illumination light with a suitably chosen wavelength.

The observation flux is then focused by a lens L5 onto a selective spatial filter 600. Behind the selective spatial filter 600, photosensitive elements 700 receive this flux after passage through spatial filter 600 which is in this case a spatial filtering hole. Each illuminated tissue micro-surface is thus conjugated with the spatial filtering element, via the optical system formed by lenses L1, L2, L3, L4 and L5. Each illuminated tissue micro-surface is thus imaged.

The filtering device 600 consists in this case of a spatial filtering hole at the limit of diffraction or slightly higher. It is intended to eliminate parasitic light emanating from the fibres lateral to the illumination fibre. The diameter of this spatial filtering hole is fixed by the characteristics of the optical system and the diameter of the fibres of the image guide. The diameter is determined in such a way that the light emanating from the illumination and reception fibre is the only light analysed. As has already been described, this filtering orifice is arranged in the conjugated or confocal plane of the tissues.

Thus, the spatial filtering device is located in a conjugated image plane at the end of the fibre-optic guide adjacent to the separator LM2. This filtering device therefore participates in the elimination of parasitic reflections and it is conjugated with the end of the fibre that is located on the detector side. This filter makes it possible to select just the illuminated fibre at a given instant. This filter is arranged in the conjugated plane of the tissues, in front of the detector that is intended to image them.

Sensor 700 is in this case a photosensitive sensor of the photomultiplier type conjugated optically with the tissue observation point. This sensor can also be an avalanche photodiode or any other detecting means permitting measurement of luminous flux. This opto-electronic receiving unit can also be made up of one or more sensors, amplified, or cooled, which make it possible to supply an electronic image.

A chromatic filtering device, if included, can make it possible to have several photodetectors which produce, in parallel, the tissue images formed by the various illumination wavelengths. For each point of the photodetector, the number of countable levels depends on the ratio between the maximum flux arriving at the detector and the parasitic flux. A 45° plate LM3 is positioned between spatial filter 600 and photodetector 700 and this deflects, to a second photodetector 900, the flux that is backscattered by the body and picked up by plate LM1, while allowing the other rays emanating from the axial view to be propagated to the axial photodetector 700.

An electronic unit 800 is positioned behind the photodetector 700 and makes it possible to process the received signal and deliver an electrical signal that is capable of controlling a visualization transmitter and/or a video recorder and/or can be processed in a microcomputer. This structure 10 makes it possible to give a dimensional image of an optical section of tissues.

By digitizing and storing sections at different depths, a three-dimensional image of the tissues or of the industrial surface under investigation is reconstituted.

Thus, photodetector 700 and device 800 together with a display monitor make up an assembly for displaying an image of the interior of the body, in which the photodetector 700 therefore constitutes an opto-electronic receiving unit permitting conversion of an optical signal to an electrical signal.

It can therefore be understood that with the device that has just been described, the illuminated surface corresponds to a point of the observed image. Movement of this illuminated micro-surface is provided by successive optical addressing of the optical fibres of the group of fibres 300. It is the juxtaposition of these various flux measurements that makes it possible to reconstitute the image.

To achieve this, the device comprises means that are able to record luminous information coming from the illuminated parts of the body during scanning and are able to record, on the basis of this luminous information, information concerning the position of the illuminated part in the scanned region, for reconstituting an image on the basis of these two sets of data.

The device that has just been described includes a selective spatial filter 600. However, within such a device, a principal filtering element is provided by confocal filtering provided by the tissue end of the fibre-optic image guide 300.

In fact, a filtering pupil is provided by the end of each fibre of image guide 300 that is located on the side of the tissues to be examined. Confocal filtering is therefore provided by the end of the guide fibre that is illuminated at instant t. Such a device can be called a "confocal or conjugated filtering device". The reduced diameter of this filtering pupil, related to the diameter of the fibre, makes it possible to eliminate the parasitic reflections that come from the adjacent fibres.

For further improvement of filtering and hence the detection of very small fluxes (of the order of nW) emanating from the tissues, the reflections that come from the two ends of the fibre-optic image guide are eliminated.

To do this, at the end on the tissue side, the fibres are cleaved or polished so as to make an angle with the plane perpendicular to the fibre axis that is sufficient to permit elimination of the reflection, which is then in so-called "leaky" mode.

More generally, the fibre end on the body side is to be made according to an end plane that is not perpendicular to a fibre outlet axis at this end. Such a plane can be made by cleavage or by polishing.

Moreover, at the end located near injection of the illumination flux, stimulation by a train of light pulses is employed for light stimulation of the source 100.

The invention described here uses an opto-mechanical scanning device that makes it possible for the various fibres making up the image guide of the endoscope to be addressed in succession. This successive addressing of the various fibres allows confocal spatial filtering of the images obtained, securing a depth resolution of the confocal microscopic type.

Since the device is confocal, in other words the illuminated spot is the optical conjugate of the source and of a detector, it recovers the rays that are reflected and backscattered by the spot that is momentarily illuminated, distinguishing these rays from the other rays arising from scattering in the tissues surrounding this spot.

The assembly formed by module 400, the image guide 300 and the deflector 200 therefore has an optical reception input formed by the lens L1, and is adjusted so that only the return rays arriving on the lens directly from the point of light concentration are transmitted to the image display means.

Module 400 therefore directs the light rays coming from the illuminated part of the region on the body-side end of the illumination fibre so that the return fibre and the illumination fibre are one and the same fibre.

This filtering is obtained here in that the optical means optically conjugate the illuminated spot to a photometric sensor, but it is possible, within the scope of the invention, to use some other means for achieving the said filtering.

Moreover, by making it possible to choose the observation plane in a diffusing environment, that is, the plane from where the signals are extracted, it permits the production of an image in three dimensions of a part of the body being examined.

In the embodiment described here, control of the emitting element 100 is adopted. According to a variant, the invention envisages interposing an optical port of the opto-acoustic or electro-optical modular type or direct control of the illumination and detection elements.

According to a variant, the means of illumination in fact comprise a source supplying trains of light pulses, and the image display means comprise means for detecting rays coming from the body, capable of temporal selection of these rays in a temporal manner adapted to the emission of light pulses.

Owing to this stimulation by a train of light pulses, the reflected flux is analysed synchronously, taking into account the transit time along the optical pathway, i.e. for the "round trip" in the optical units, image guides and tissues.

Thus, the reflected signals arriving at photodetector 700 roughly simultaneously with the emission of illumination by source 100 are analysed relative to this emission.

The delay command between emission and reception is provided by an electronic control device. The times for the duration of the illumination pulses are correctly calculated and adjusted for each length of image guides and each type of optical device. Any residual fluxes coming from defective optical ports are eliminated by a polarizing device between emission and reception.

Thus, in the variant cited above, an optical and/or electronic port device controlled by the control device 800 makes it possible to perform synchronized detection of the reflected flux. Accordingly, parasitic reflected rays are not processed.

The control device 800 preferably includes a unit for generating the sequence of all the events and for processing all the signals emitted by sensors and possibly from various elements modulating the illumination flux or emanating from the elements for controlling reception amplification.

This clock device controls the synchronous detection ports so as to take account of scanning of the various fibres and of the optical transit time between the sources and the flux analysers.

More precisely, in the present preferred variant, the control module 800 positions, as described previously, deflector 200 in successive positions each corresponding to a different fibre of the group of fibres 300.

For each position of the deflector, it deflects the illumination beam onto lens L4 so that the said beam leaves the said lens again opposite a chosen fibre and in alignment with the said fibre.

After passing through the fibre, this beam impinges on the body being observed and, after being backscattered by the tissues and after passing through the fibre in the opposite direction, it reemerges from the same fibre at the same angle as the illumination beam, travels the same path as the illumination beam through lens L4 and deflector 200, and is thus directed onto a filtering hole 600.

For each of its positions, deflector 200 directs the illumination beam onto a chosen fibre then recentres and realigns the return beam, without changing position.

According to a preferred arrangement, an optical fibre is used for each pixel for displaying the image on a video screen, and the deflector adopts scanning synchronized with scanning effected by scanning means of the video screen.

In other words, deflector 200 remains on a fibre for an interval of time dictated by the duration of a video screen pixel.

This time interval is divided advantageously into two separate half-intervals without any intermediate interval, corresponding respectively to a first phase of illumination of the body by the source and a second phase of reception of the light backscattered from the body to photodetector 700.

To make use of these two phases without interfering crossing of the light and without leaving an interval of non-use of the fibre between the two phases, a fibre length is chosen such that the duration of a round trip of the light is equal to half the duration that the deflector is positioned opposite the fibre.

Thus, the backscattered light, which begins to arrive on deflector 200 after performing a round trip, begins to arrive at the end of the first half of the interval of positioning of deflector 200, the instant when emission of the illumination beam is stopped.

The instant situated at the half-interval of positioning of deflector 200 therefore corresponds simultaneously to disappearance of the illumination beam and to appearance of the return beam at the deflector.

We thus avoid crossing of the light at the end of the fibre that is adjacent to the deflector, which would give rise to a strong parasitic light, while benefiting from the total positioning time of deflector 200, since the parts close to the deflector are at any moment traversed by a beam that is being used, in the forward direction and then in the return direction.

For the pixel durations of existing video screens, the said fibre length is of the order of 10 meters.

Accordingly, fibres are used whose length greatly exceeds the lengths dictated up to now by the dimensions of the body to be observed. The fibres are coiled so that they take up less space.

Use of an optical heterodyne device, an interferometry device or a spectrometry device is envisaged according to a variant of the invention.

All of the devices described above make it possible to obtain reflected fluxes that are of the order of 1/106 of the parasitic flux emitted from the various surfaces of the optical architecture.

In a particular arrangement of the apparatus and when the reflected fluxes are less than 1 nW, a fibre-optic branch equipped with a mirror with adjustable distance can provide optical heterodyne amplification based on the principles of interferometry.

The device described above makes it possible to locate tissues at an angle of $20°\times20°$ and display confocal microscopic optical sections at an angle of $10°$. In parallel with this confocal microscopic optical section, the investigator has a wide-field axial view that enables him to "get his bearings".

Wide-field examination is effected by means of lenses L3, L1 and L5 following the rules of the art for supplying an image of the order of 2 to 3 cm in the image plane of lens L5. It is lens L5 that focuses the flux onto the detector. The said examination represents of the order of $40°$ of field. The complete image formed is refreshed 25 times/second for $100\times100$ resolved points. Therefore a so-called "flying spot" technique is used here.

In a tissue image of $100\times100$ dots covering a field of 400 $\mu$m, the resolution is 4 $\mu$m.

The fact that the same optical fibre is used for illumination and observation offers many advantages.

Thus, in contrast to the known devices, the fact that the rule of separation of the illumination and observation pupils is not employed means that it is possible to use an optical pupil that permits a large numerical aperture. Such a set-up therefore permits very good image resolution, which is determined purely by the quality of the guide used. This guide quality depends on its particular characteristics, and especially the fibre diameters used.

Use of the same optical fibre for illumination of the tissues and analysis of the reflected flux permits conjugation between the source spot and the point of spatial filtering of the reflected flux, which is always ensured without the need for adjustment since the source spot, or illuminated spot as well as the point of spatial filtering, or observed spot, depend on the same optical element, i.e. in particular the same outlet lenses but especially the same optical fibre.

More generally, the use of optical fibres permits remote arrangement of the illumination device 100 and scanning device 200 and the detection device 600, 700, 800 while preserving a point-by-point mode of analysis of the "flying spot" type.

The fact that optical fibres are used makes it possible to achieve independence between the observed field, the numerical aperture and the position of the plane of observation on the Z axis, i.e. the axial position in depth.

The device for modulating the illumination beam, the device for reflection and for scanning of the fibres, permitting synchronized detection, can also be located remotely. The control electronics and the various bulky optical components are also far away from the tissues being examined. Moreover, the part located in front of the tissue to be examined is of very small volume (a few mm3 to a few cm3).

One benefit of using a fibre-optic image guide is therefore to be able to transport the sources, the deflectors performing two-dimensional scanning of the illumination and observation field. This arrangement determines miniaturization and the use of devices located in front of the tissues in all positions.

Keeping the same system of image guides, whichever field is to be observed, makes it possible to preserve the focusing characteristics of the plane of observation.

One of the characteristics of the invention described in this device consists of simultaneous axial observation of the images with a large field and lateral observation with a small field and high resolution. While one of the wavelengths is used for axial observation, the other is used for the confocal microscopic section. It is therefore possible to display the axial image and the confocal optical section simultaneously on two different screens.

Two optical devices are therefore combined so as to give a macroscopic axial image and a microscopic lateral image.

One of the benefits of the invention is the use of optical fibres for which the choice of materials and their machining contributes to defining the numerical aperture, whereas the field of view is fixed by the focal length of the lenses located in front of the tissues.

By changing the numerical aperture of the fibre and/or the limiting diameter of the illumination beam, it is possible to alter the aperture of the optical system and therefore change the spatial resolution. Furthermore, altering the diameter of the fibres makes it possible to change the thickness of the optical section without the proviso of keeping the same magnification.

Thus, we have just described a device with which it is possible to obtain performance at least identical to the conventional devices with a greatly reduced overall size, as the same image guide assembly is used for illumination and for analysis of the tissue reflection.

Of course, the invention is not limited to the example that has just been described.

According to a variant of the invention of miniaturized type, the required optical path is obtained by folding the bundle. The losses this produces are then compensated by increasing the power of the source while observing the limits in the AFNOR and ANSI standards.

Moreover, the example of embodiment of the invention described above has been presented as being intended for the examination of biological tissue. Using a device according to the invention, any other surface can be investigated, notably in an industrial setting, in real time. The invention therefore relates both to the examination of manufactured devices and examination of living organisms, or even investigation of the interior of mineral substances.

The invention is not limited to applications in medicine and in biology but is also intended for any type of investigation, especially in an industrial environment, for example the inspection of pipelines or turbines in a polluting environment and/or where they are inaccessible to direct observation, and more generally in environments that are hostile to humans, and more generally the observation of any other surface.

According to the invention, all of the electronic and mechanical elements and more generally all elements that are attracted or are likely to be attracted by a magnetic field are placed advantageously at the end of the guide that is opposite to the patient.

The materials intended to be in contact with the tissues are selected so as not to disturb the magnetic fields. As the part near the patient is not attracted by a magnetic field, it can be placed under a device for observation by magnetic resonance imaging (MRI) so as to be able to carry out simultaneous, combined observations by endoscopy and MRI.

This device permits remote observation of tissues, and the length of the image guide of several meters makes it possible to carry out confocal microscopic imaging for endoscopy, while at the same time performing a study by nuclear magnetic resonance.

In the preferred embodiment of the invention, an operator gains access to the tissues with another optical instrument such as a photo-coagulation laser while making use of the image guide 300.

The light source unit 100 is in that case able to supply on command a particularly energetic beam, which produces a treatment or a transformation, in this case photo-coagulation, on the tissues (more generally the material of which the observed body is constituted). The treatment can also be photo-destruction, or more generally a photon therapy treatment when using the device on a living body.

The electronic control module 800 includes a fibre selection module for controlling the source unit 100 in relation to the position of deflector 200.

On the display screen, the user indicates a window or region, contained within the image shown on the screen, on which he wishes to effect the treatment.

As the image shown corresponds to all of the fibres of the group of fibres 300, the region indicated by the user corresponds to a subgroup of fibres which the selection module deduces automatically from the indication given by the user.

The references of the selected fibres are taken into account by the control unit 800, which operates the source unit 100 in relation to the position of deflector 200 in the course of ordinary scanning, in such a way that unit 100 supplies a particularly energetic beam, in this case a therapeutic laser beam, when deflector 200 is directed onto one of the selected fibres, and in such a way that unit 100 only supplies an ordinary illumination beam when the deflector is directed towards a fibre that has not been selected.

According to the present embodiment, source unit 100 comprises two sources 110 and 115, one 110 for treatment (e.g. laser) and the other 115 for simple illumination, module 800 activating one or the other depending on the fibre illuminated.

According to a variant, a single source is used, which can on command emit a more or less powerful beam depending on the fibre illuminated, with or without a treatment effect depending on the beam power.

Such a device also employs a module for processing the electrical signals supplied by photodetector 700 which is controlled by module 800, synchronized with the position of deflector 200, for applying particular processing to the beams received from selected fibres and thus compensate the highest intensity received from the parts during treatment.

The treatment light is thus also used as the illumination light, which is analysed after backscattering.

Therefore the same fibre is used here each time for simultaneously conveying the treatment light, the illumination light and the returning observation light.

According to one variant, a different fibre is used for conveying the observation beam and the treatment beam.

Here the same fibre is used both for observation and for treatment, which may be therapeutic.

According to another variant, the same fibre also carries a signal used by a device for spectrometric analysis, for example for the purpose of diagnosis. A device combining these three functions then carries, on the same image guide, signals used for three purposes: observation, diagnosis and treatment.

What is claimed is:

1. A device for observing the interior of a body, comprising:

display means for displaying an image;
   a group of fibers gathered together side by side and intended to pass through an internal part of the body for conveying an image from the interior of the body to the display means, the group of fibers forming an image guide, the ends of which are arranged in the same order at two ends of the guide;
   illumination means for scanning the body that scans the fibers of the group of fibers, the illumination means being placed at the end of the fibers that is farthest from the body,
   the illumination means including,
      means for imparting successive angular deflections to an illuminating beam, and
      means for converting the angular scanning obtained to a lateral scanning relative to a principal entry axis of the group of fibers; and
   means for collecting, on the body side, light emitted from scanning of the body and for transmitting the collected light to the image display means, so that the collected light constitutes, at least partially, the image displayed,
   wherein each of the illuminated fibers is also used for conveying a return beam originating from the region of the body illuminated by it, and in that the means for imparting successive angular deflections of the illuminating beam are arranged to cause a return beam emerging from this same fiber to travel along the same optical path as that of the illuminating beam entering the said fiber.

2. The device according to claim 1, further comprising a section for detecting a return beam emerging from the group of fibers, which comprises a filtering device including a filtering hole arranged in a plane conjugated with the plane where the light emerging from the end of the group of fibers closest to the body is focused.

3. The device according to claim 1, wherein for each successive angular deflection, a fiber corresponding to this deflection has a length such that the round-trip propagation time of the light in fiber is equal to half the time during which the illuminating means maintains the said angular deflection, and the illuminating means illuminate the fiber during the first half of the time interval in which the illuminating means maintains the said angular deflection.

4. The device according to claim 1, wherein the display means comprises two image display devices, one adapted for presenting a view of a general region and the other a microscopic view of a more restricted region and in that it includes means for simultaneously displaying the two views on the two image display devices.

5. The device according to claim 1, wherein the illuminating means are provided for illuminating the fibers with a light that produces a transformation of the body substance.

6. The device according to claim 5, wherein the image display means include means enabling a user to select, on the image displayed, a region to be treated, these means being provided for converting the indication of this region into references of fibers and for commanding the illuminating means to illuminate the fibers corresponding to these references with the light producing the said transformation.

7. The device according to claim 1, further comprising means for producing, in the swept region of the body, a point of concentration of the illuminating light rays.

8. The device according to claim 7, further comprising means for adjusting the depth position of the point of concentration of the light rays as well as means for storing the images received for different settings of depth position in order to supply a three-dimensional image of the observed part of the body.

9. The device according to claim 8, wherein the means for concentrating the rays are positioned at the body-side end of the image guide and in that the means for adjusting the depth position of the point of concentration are constituted by means for setting the distance of the means of concentration relative to the body-side end of the image guide.

10. The device according to claim 7, further comprising means that have an optical reception inlet, these means being able to transmit, to the image display means, just the signals obtained from direct light rays between the point of concentration and the optical reception inlet.

11. The device according to claim 7, wherein the means for concentrating the light rays and the said means at reception inlet are formed by the same module, the illumination beam and the return beam having the same path within this module.

12. The device according to claim 1, wherein the means for illuminating the fibers successively are provided for illuminating one fiber at a time.

13. The device according to claim 1, further comprising means for recording luminous information originating from illuminated parts of the body in the course of scanning and for recording, on the basis of this luminous information, information on the position of the part illuminated in the swept region, for reconstituting an image on the basis of these two sets of data.

14. The device according to claim 1, wherein the body-side end of at least one optical fiber forms a plane that is not perpendicular to the outlet axis of the fiber.

15. The device according to claim 1 adapted for observing the interior of the body of a living being.

16. The device according to claim 1 adapted for observing the interior of a manufactured device.

* * * * *